United States Patent [19]

Ohsaki et al.

[11] Patent Number: 4,525,482

[45] Date of Patent: Jun. 25, 1985

[54] PROCESS FOR PRODUCING A GAS CONTAINING METHANE

[75] Inventors: Kozo Ohsaki, Funabashi; Katsutoshi Kikuchi, Chiba; Yoshitsugu Hirota, Mobara, all of Japan

[73] Assignee: Toyo Engineering Corporation, Tokyo, Japan

[21] Appl. No.: 592,153

[22] Filed: Mar. 22, 1984

[30] Foreign Application Priority Data

Mar. 23, 1983 [JP] Japan ................................. 58-48372

[51] Int. Cl.$^3$ ................................................ C07C 1/04
[52] U.S. Cl. .................................... 518/707; 518/706; 518/708; 518/711; 518/712; 518/713; 518/714; 518/715; 48/197 R; 422/200; 422/190; 422/193; 422/211
[58] Field of Search ............... 518/706, 707, 708, 711, 518/712, 713–714, 715; 48/197

[56] References Cited

U.S. PATENT DOCUMENTS 2,662,911 12/1953 Dorschner et al. ................. 518/712
2,852,545 9/1958 Jenny ................................... 518/712

*Primary Examiner*—Howard T. Mars
*Attorney, Agent, or Firm*—Flynn, Thiel, Boutell and Tanis

[57] ABSTRACT

This invention provides an improved, simple and energy saving process for producing a gas containing methane, which process utilizes a reactor having a catalyst bed of a structure wherein a synthesis gas is allowed to pass perpendicularly to the longitudinal directions of a plurality of cooling tubes installed vertically within the catalyst bed. Within the cooling tubes, a liquid coolant at its boiling temperature is flowed upwardly under pressure. A portion of the reaction product gas leaving the catalyst bed is mixed, without cooling, with fresh feed gas and is recirculated to the catalyst bed. The amount of the recycled gas is less than 5 times the amount of fresh feed gas. The foregoing process produces a product gas containing methane from a feed gas containing carbon monoxide and hydrogen.

16 Claims, 11 Drawing Figures

PROCESS FOR PRODUCING A GAS CONTAINING METHANE

FIELD OF THE INVENTION

This invention relates to a process for producing a gas containing methane from a starting gaseous mixture (feed gas) containing carbon oxides and hydrogen. More specifically, this invention relates to a process for producing a gas containing methane utilizing a reactor having a fixed catalyst bed. Within this reactor, a feed gas is flowed through the catalyst bed in a direction perpendicular to a plurality of cooling tubes which are vertically disposed in the catalyst bed. A liquid coolant under pressure continuously flows upwardly through the tubes. The temperature of the catalyst bed is maintained at a relatively low level by the cooling effect of the cooling tubes, whereby a product gas containing methane is produced from a feed gas containing carbon oxides and hydrogen.

BACKGROUND OF THE INVENTION

The so-called methanation reaction, in which carbon monoxide and hydrogen are reacted to produce methane, has been conventionally utilized for the purpose of converting carbon monoxide, which is a poison to the catalysts used for an ammonia synthesis reaction, to methane, which does not poison the ammonia synthesis catalyst. Recently, the use of the methanation reaction as a means for producing a gaseous mixture enriched with methane, a fuel gas for industrial or domestic use, has been studied. The gaseous mixture enriched with methane is produced from a starting gaseous mixture consisting essentially of carbon oxides and hydrogen produced by the gasification of lower grade fuels, such as coal or heavy oil.

The methanation reaction employs hydrogen and either or both of carbon monoxide and carbon dioxide as starting materials, and proceeds, in the presence of a suitable catalyst, in accordance with the following equations:

$$CO + 3H_2 = CH_4 + H_2O \qquad (1)$$

$$CO_2 + 4H_2 = CH_4 + 2H_2O \qquad (2)$$

$$CO + H_2O = CO_2 + H_2 \qquad (3)$$

All of these reactions, of which reaction (1) is generally considered the main reaction and the reactions (2) and (3) are considered side reactions, do not proceed satisfactorily toward the right side of the respective equations due to the chemical equilibria established when the reaction temperature is high. Moreover, the reactions according to the equations (1) and (2), as is known in the art, are accompanied by generation of a very large amount of heat (exothermic reaction heat).

Several processes are disclosed in U.S. Pat. No. 4,130,575, British Pat. No. 1 516 319, and Japanese Pat. Laid-Open No. 82188/1980 for effecting methanation according to the foregoing reactions on a large scale. All of the foregoing prior art processes are two-stage reaction processes wherein an adiabatic reactor is used as a first reactor to which a feed gas is supplied, and the feed gas, after having undergone partial methanation in the first reactor, is then flowed through a second reactor to complete the methanation reaction. In these known processes, the amount of reaction heat generated in each of these reactors is controlled by recirculating a considerable portion of the reaction product gas, which is discharged from the catalyst bed of the first or second reactor and then cooled, to the inlet of the catalyst bed of the first reactor.

In these known processes, some of the heat of reaction is lost when the reaction product gas is cooled and recirculated, and it is further necessary to use a second reactor for the purpose of further effecting the methanation reaction and thereby lowering the content of carbon monoxide in the final product gas. The carbon monoxide content of the product gas produced by the first reactor used in these prior art processes is high due to the high temperature of the adiabatic catalyst bed of the first reactor, and to the chemical equilibrium relationships established by the foregoing three chemical reactions at such high temperature. Accordingly, these conventional methanation processes involve the drawbacks that a large part of the reaction heat cannot be recovered in the form of valuable high temperature, heat energy and that complex process equipment is required.

SUMMARY OF THE INVENTION

The present invention provides a process for ameliorating the drawbacks of the conventional processes, in which process a single reactor having one or more catalyst beds, in each of which cooling tubes are vertically disposed, is maintained at a relatively low temperature by strong indirect cooling to thereby carry out the methane-producing reactions more completely than occurs in the conventional processes. A portion of the gas discharged from the catalyst bed, or from one or more catalyst beds if a series of catalyst beds is employed, is recirculated, without cooling, to the reactor. The molar amount of the recirculated gas is less than 5 times the molar amount of fresh feed gas that is supplied to the inlet of the catalyst bed or to the first catalyst bed of a series of catalyst beds. The process of the present invention attains the objects of the invention mainly by the following two means:

(1) A synthesis gas comprising a mixture of fresh feed gas and recycled gas is continuously flowed substantially horizontally through a catalyst bed of such a structure that the synthesis gas flows at right angles to the longitudinal directions of cooling tubes installed vertically within the catalyst bed of a methane synthesis reactor. At the same time, a liquid coolant at its boiling temperature is continuously flowed upwardly under pressure through the cooling tubes. The synthesis gas contains hydrogen and one or more carbon oxides, preferably carbon monoxide and carbon dioxide, as well as a substantial amount of methane.

(2) A product gas recycle stream comprising a portion of the total reaction product gas leaving the catalyst bed, hereinafter referred to as the recycle gas, is recirculated, without cooling, to the inlet of the catalyst bed and is admixed with fresh feed gas, hereinafter referred to as the feed gas. The molar amount per unit time of the recycle gas fed into the reactor is less than 5 times the molar amount per unit time of the fresh feed gas fed into the reactor. The mixture of feed gas diluted with recycle gas is supplied to the inlet of the catalyst bed. In embodiments where several catalyst beds are employed in series within a single reactor, the recycle gas can be the gas discharged from one or more of the catalyst beds, and it is recirculated to the first catalyst bed in the series.

The principal objects of the process of this invention are to obtain a product gas which comprises methane by a simple process, and to recover the heat evolved by the reactions which produce the methane by heat transfer to a liquid coolant whereby to generate a large quantity of high pressure vapor of the coolant.

A further object of this invention is to reduce the power required for recirculating a portion of the gas discharged from the outlet of the catalyst bed to the inlet of the catalyst bed.

Other objects, features and advantages of the present invention will become apparent from the following description and the appended claims, taken in conjunction with the accompanying drawings.

DETAILED DESCRIPTION OF THE INVENTION

According to this invention, the synthesis gas is flowed substantially perpendicularly to the longitudinal axes of a plurality of parallel, spaced-apart cooling tubes installed vertically in the catalyst bed. A liquid coolant, at its boiling temperature and under pressure, is continuously flowed upwardly within the tubes so that the overall coefficient of heat transfer of the heat flow emanating from the catalyst bed to the liquid coolant is thereby increased. Further, the vaporization of the liquid coolant in the cooling tubes is thereby facilitated so that the cooling effect on the catalyst bed and the synthesis gas undergoing the reaction is increased to a large extent. However, even with such means, the catalyst bed and the synthesis gas cannot be maintained at a satisfactorily low temperature. Consequently, in this invention, a portion of the product gas, which has an increased methane concentration and a decreased carbon monoxide concentration as a result of the methanation reactions, is recirculated to the inlet of the catalyst bed without being cooled. The maximum amount of the recycled gas that is recirculated to the catalyst bed is 5 moles per unit time for each 1 mole per unit time of the fresh feed gas that is fed to the catalyst bed. By this means, the concentration of carbon oxides in the synthesis gas fed to the inlet of the catalyst bed is reduced so that the evolution of reaction heat is controlled as the methanation reaction is carried out.

By the combined effects of the directions of flow of the liquid coolant in the cooling tubes and the synthesis gas in the catalyst bed, together with the recirculation of a portion of the product gas as described above, the gas passing through the catalyst bed is efficiently cooled, whereby the temperature of both the gas and the catalyst can be maintained in the range of from 240° C. to 600° C., preferably 240° C. to 380° C. This allows the greater part of the reaction heat to be recovered as high pressure vapor of the liquid coolant, a result not achieved by conventional processes.

The invention will be described in detail below with reference to the accompanying drawings.

Figure 1:
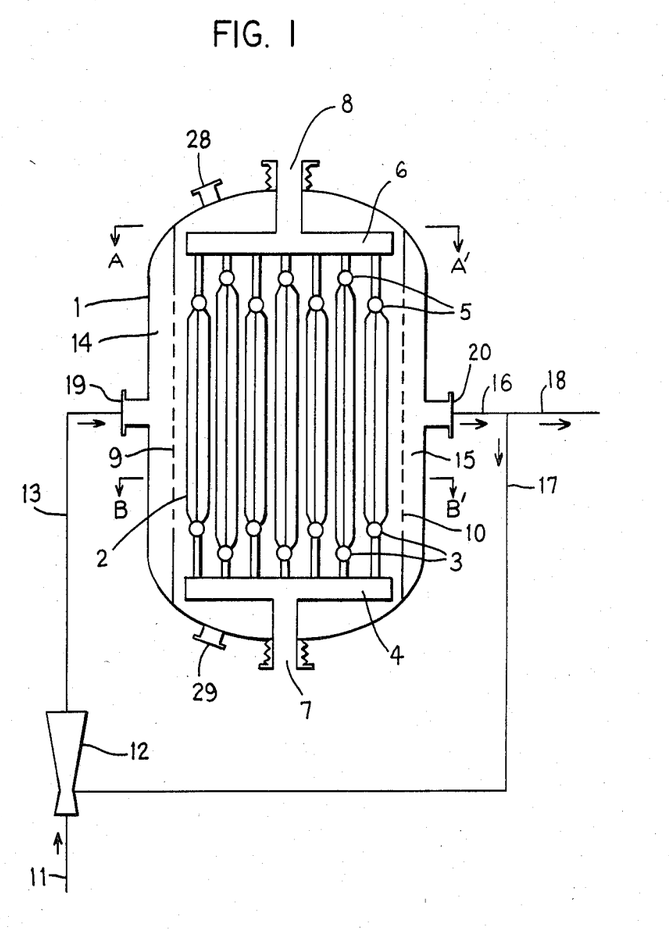
FIG. 1 is a schematic diagram showing an embodiment of the process according to the present invention, including a schematic vertical cross-sectional view of a reactor used in the present invention.
Figure 2A:
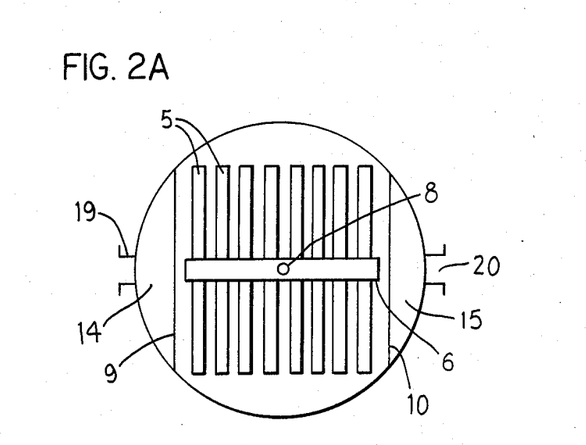
FIGS. 2A and 2B are schematic horizontal cross-sectional views taken along the lines A–A' and B–B' of the reactor shown in FIG. 1.
Figure 2B:
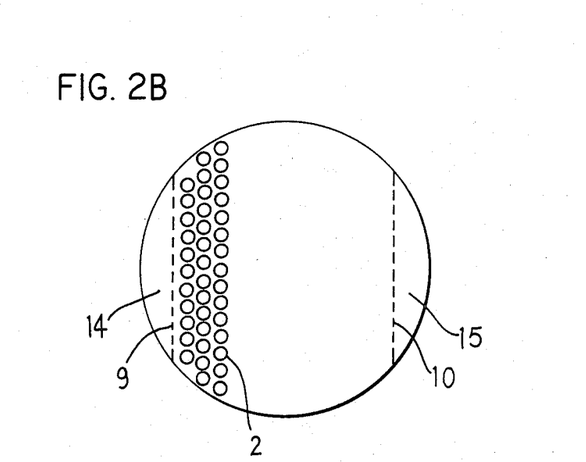

FIG. 1 is a schematic diagram showing an example of the process according to this invention. More specifically, FIG. 1 illustrates a process example wherein a reactor 1 is employed. Horizontal cross sections of the reactor 1, taken along the section lines A–A' and B–B', are shown in FIGS. 2A and 2B, respectively. In FIG. 2B, only a portion of the total number of cooling tubes 2 are shown.

The reactor 1 includes a plurality of vertically disposed cooling tubes 2 which are provided in a plurality of spaced-apart linear rows (FIG. 2B) in the catalyst bed comprising the catalyst-packed space between the gas permeable catalyst retainers 9 and 10. A liquid coolant at its boiling temperature is flowed upwardly through the tubes 2 under a desired pressure. The coolant is fed into the reactor from an inlet 7 and is discharged from the reactor through an outlet 8. The liquid coolant supplied from the coolant inlet 7 is distributed by a primary distribution header 4 to a plurality of secondary distribution headers 3 located upwardly from the primary distribution header 4. The secondary distribution headers 3 comprise a plurality of essentially horizontal, parallel tubular members. The arrangement thereof is essentially the same as the arrangement of the collection headers 5 shown in FIG. 2A. The liquid coolant which flows into the secondary distribution headers 3 is distributed by each header 3 to a multiplicity of the cooling tubes 2. The lower ends of the tubes 2 in each row communicate with an associated secondary distribution header 3. The liquid coolant then flows upwardly through the hollow interior of each of the tubes 2, and absorbs reaction heat evolved in the catalyst bed surrounding the tubes. The absorption of this reaction heat causes the liquid coolant to boil and pass upwardly through the cooling tubes 2 as a vapor-liquid mixture comprising the liquid coolant in both vapor and liquid form. The vapor-liquid mixture flows upwardly in the cooling tubes 2 and is collected at the top ends thereof by a plurality of secondary collection headers 5, each header 5 being in communication with a number of the tubes 2. Thus, each row of tubes 2 within the catalyst bed is in communication with a single distribution header 3 and collection header 5. The coolant then flows to a primary collection header 6 and passes out of the reactor via the coolant outlet 8.

Outside of the reactor, the mixture of the liquid coolant and coolant vapor is separated by a separator (not shown). The liquid phase coolant is recirculated to the coolant inlet 7 by appropriate transport means without cooling, while the coolant vapor is utilized for a desired purpose, such as generation of electricity by a turbine. Systems for supplying and recycling the coolant in the manner described above are well known.

A fresh feed gas containing hydrogen, carbon monoxide, carbon dioxide and optionally methane is supplied from a conduit 11 and is mixed with a recycle gas which is recirculated through a conduit 17. The recycle gas contains hydrogen, carbon dioxide, methane and a small amount (preferably less than 0.1 wt. %) of carbon monoxide. The feed gas supplied from the conduit 11 may further be mixed with pressurized steam. The resulting mixture is pressurized by a booster 12. The pressurized synthesis gas is then injected into a conduit 13 and enters an inlet flow passage 14 of the reactor 1 through the gas inlet 19. From the flow passage 14, the gas passes uniformly through a first gas permeable catalyst retainer 9, and then flows substantially horizontally through a catalyst bed packed around the cooling tubes 2, which catalyst bed is provided in the space between the first catalyst retainer 9 and a second gas permeable catalyst retainer 10. As the gas passes through the catalyst bed, the methanation reaction is effected. The gas then passes out of the catalyst bed through the catalyst retainer 10, then enters an outlet flow passage 15, and then leaves the reactor through the gas outlet 20 as product gas. From the outlet 20 the product gas passes through a conduit 16. Part of the product gas is recirculated to the booster 12 by a branch conduit 17, while the remainder of the product gas is discharged out of the system as a final product gas through an outlet conduit 18.

As the synthesis gas passes through the catalyst bed, the methanation reactions occur and the heat thereby evolved, as described above, is absorbed by the liquid coolant and effects generation of coolant vapor. A catalyst charging inlet 28 and a catalyst discharge outlet 29 are provided at the top and bottom, respectively, of the reactor 1 for loading and discharging the catalyst.

FIGS. 3A-3D and 4-7 are schematic drawings showing examples of reactors having multiple reaction chambers which can be used to carry out the process of the present invention. Such reactors are described in U.S. patent application Ser. No. 530,298, filed Oct. 31, 1983, the entire contents of which are hereby expressly incorporated by reference in the present application.

Figure 3A:
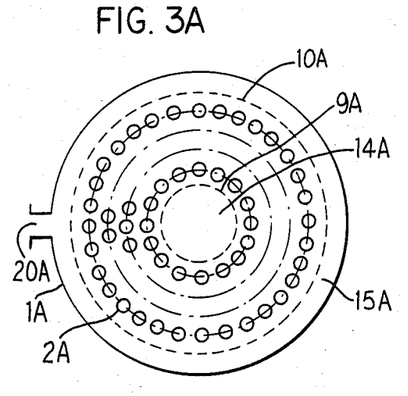
FIGS. 3A through 3D are schematic horizontal cross-sectional views taken along lines A–A', B–B', C–C' and D–D' in FIGS. 4–7, respectively, of reactors useful in the present invention and showing different ways of subdividing the catalyst bed into a plurality of reaction chambers.
Figure 3B:
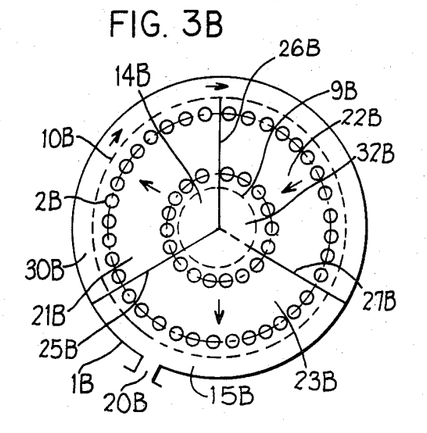
Figure 3C:
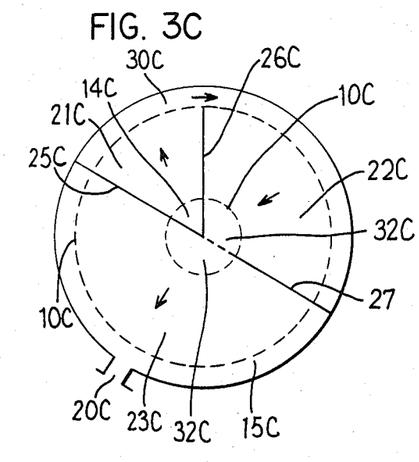
Figure 3D:
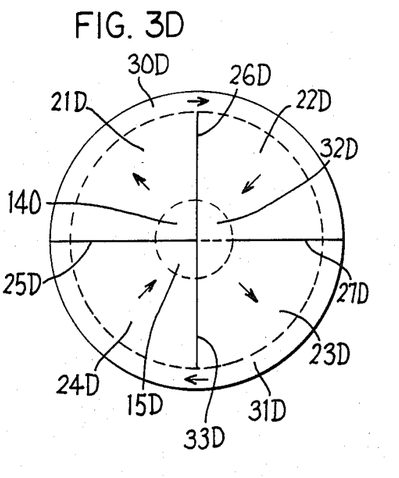
Figure 4:
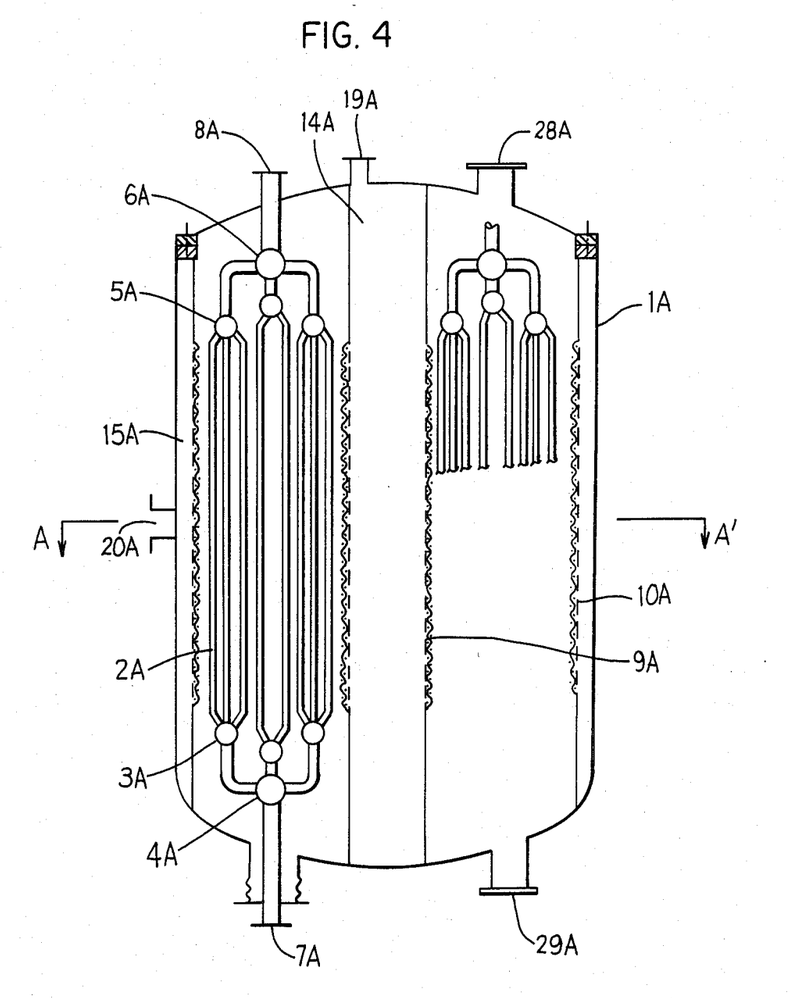
FIGS. 4–7 are schematic vertical cross-sectional views of further reactors that can be used to carry out the process of the invention.
Figure 5:
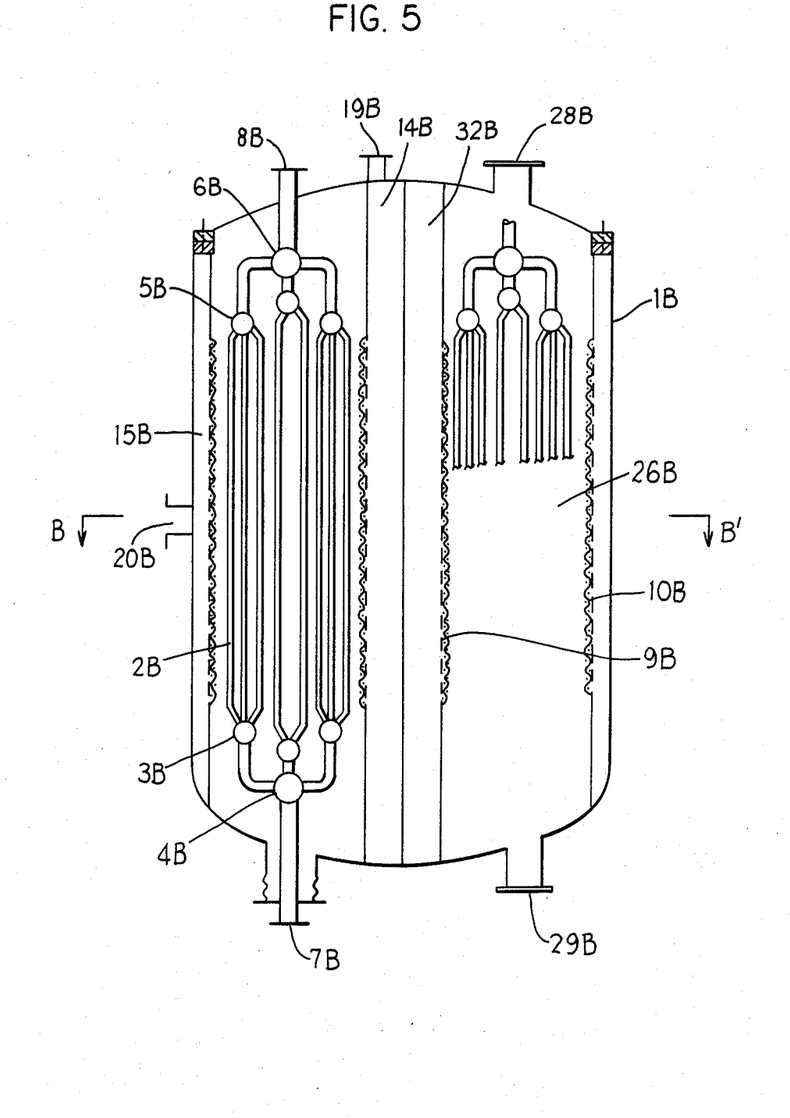
Figure 6:
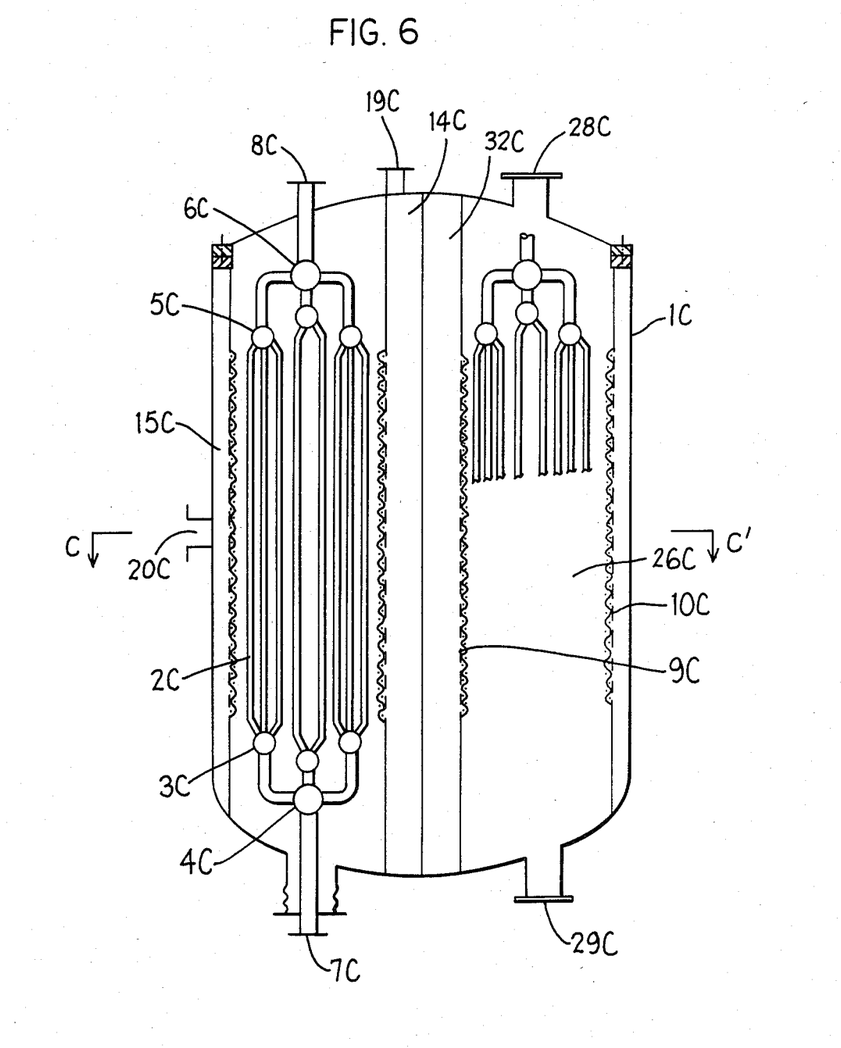
Figure 7:
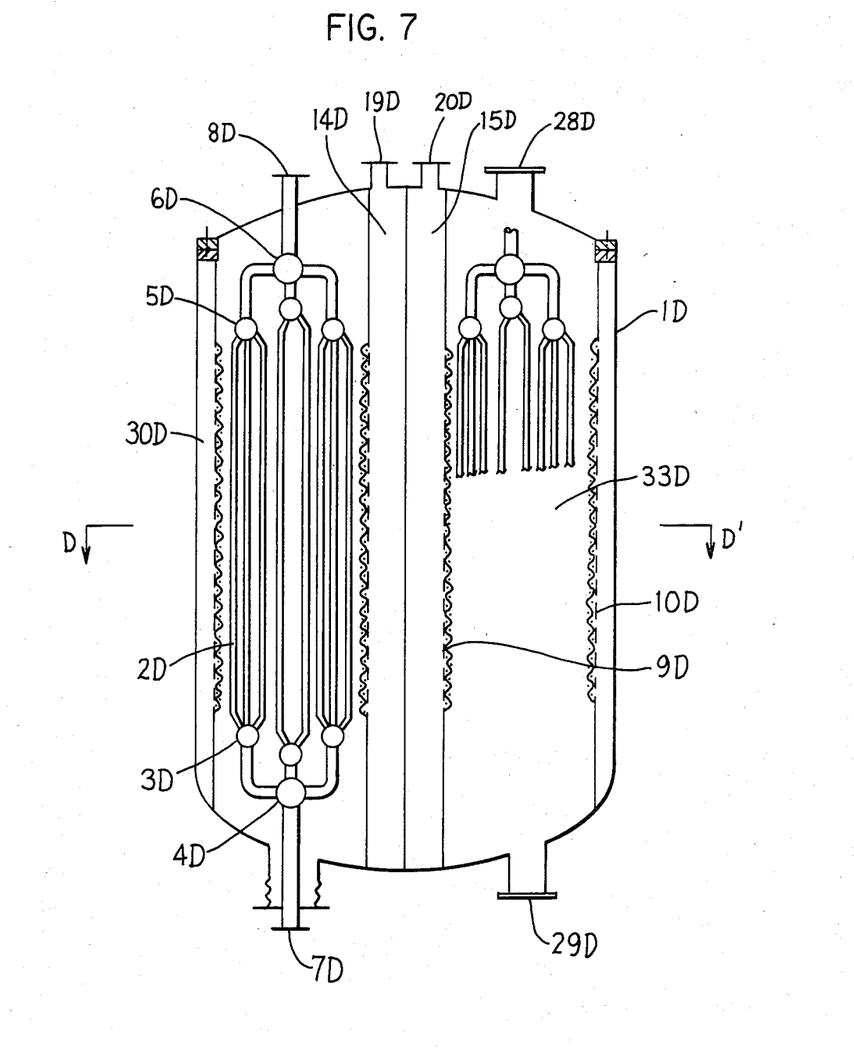

In each of the embodiments shown in (1) FIGS. 4 and 3A, (2) FIGS. 5 and 3B, (3) FIGS. 6 and 3C, and (4) FIGS. 7 and 3D, respectively, a description of the parts which function in the same manner as those described in the first embodiment of the invention shown in FIG. 1 will be omitted to simplify the description. Such corresponding parts are identified by the same reference numerals as in FIGS. 1, 2A and 2B, with the suffixes A, B, C or D added thereto, respectively.

The reactor 1A shown in FIGS. 3A and 4 is a radial flow reactor wherein the synthesis gas flows radially outwardly through an annular catalyst bed located within an intercylinder spaced defined by coaxial, inner and outer, cylindrical gas permeable catalyst retainers 9A and 10A. The cooling tubes 2A in this reactor are arranged in concentric circles coaxial with the common axis of the catalyst retainers 9A and 10A. The primary distribution header 4A, secondary distribution headers 3A, secondary collection headers 5A, and primary collection header 6A are similar to the ones employed in the first embodiment of the invention shown in FIG. 1, except that these headers 3A, 4A, 5A and 6A are either ring-shaped or of arcuate shape.

As shown in FIGS. 3A and 4, the synthesis gas enters the reactor 1A through a gas inlet 19A located near the center of the reactor 1A on the top thereof, passes into an inner flow passage 14A defined by the interior of the catalyst retainer 9A, and then flows radially outwardly through the gas permeable inner catalyst retainer 9A. The synthesis gas then flows radially in all directions and substantially horizontally from the inside to the outside of the catalyst bed packed around the cooling tubes 2A in the intercylinder space between the catalyst retainers 9A and 10A. The gas then leaves the catalyst bed through the outer catalyst retainer 10A and enters an annular outer flow passage 15A. Finally, the gas leaves the flow passage 15A through an outlet 20A formed on the side of the reactor 1A.

In the foregoing embodiment, the cooling tubes 2A are arranged on a multiplicity of coaxial circles as shown in FIG. 3A, and the headers 3A, 4A, 5A and 6A are appropriately ring-shaped or curved. Since the synthesis gas flows essentially at right angles to the longitudinal directions of the cooling tubes 2A, in the same manner as in the first embodiment shown in FIG. 1, the overall heat transfer coefficient of the heat flow from the catalyst bed to the coolant through the thickness of the cooling tubes 2A can be maintained at a high level. Although it is possible to flow the synthesis gas, in the embodiment shown in FIGS. 3A and 4, in the opposite direction, that is, radially inwardly through the annular catalyst bed, it is usually advantageous to pass the synthesis gas radially outwardly through the catalyst bed to facilitate the methanation reaction.

FIGS. 3B and 5 illustrate a third embodiment of a reactor useful in the process of the present invention wherein the annular catalyst bed shown in FIG. 3A is partitioned vertically by three radially extending partition walls 25B, 26B and 27B, thereby defining three reaction chambers 21B, 22B and 23B each containing a separate catalyst bed. In this embodiment, the synthesis gas enters the reactor 1B via a gas inlet 19B and enters a longitudinally extending gas flow passage 14B between the partition walls 25B, 26B and the inner catalyst retainer 9B. The inlet 19B is provided at the top or bottom of the reactor. In the embodiment shown in FIG. 5, the gas inlet 19B is formed at the top of the reactor near the center thereof.

The flow path of the synthesis gas in the reactor 1B is indicated by the arrows in FIG. 3B, and is similarly indicated in the additional embodiments of FIGS. 3C and 3D discussed below. The synthesis gas flows radially outwardly from the flow passage 14B successively through the inner catalyst retainer 9B, first catalyst bed 21B, and outer catalyst retainer 10B. The synthesis gas thereupon enters an outer gas flow passage 30B, in which the gas flows clockwise as indicated in FIG. 3B, and then passes radially inwardly through the outer catalyst retainer 10B, second catalyst bed 22B and inner catalyst retainer 9B to thereby enter a second inner flow passage 32B. The synthesis gas moves clockwise within the flow passage 32B and then flows radially outwardly through the retainer 9B, third catalyst bed 23B and outer retainer 10B to thereby enter an outer gas flow passage 15B. The thus-formed product gas then leaves the reactor through the product gas outlet 20B.

The vertical division of the catalyst bed into three catalyst beds as described above increases the velocity of the gas flowing in each catalyst bed and also increases the overall coefficient of heat transfer relative to the coefficient of heat transfer achieved in the embodiment shown in FIG. 3A. When the catalyst bed is subdivided as shown in FIG. 3B, the distribution and collection headers can be grouped by reaction chamber and operated independently for each reaction chamber. When independent distribution and collection headers are installed for each reaction chamber, the pressure of the liquid coolant can be controlled separately for each reaction chamber. By this means, in the reaction chamber where the reaction occurs most vigorously and generates a large amount of heat, it is possible to maintain the temperature of the coolant at which the coolant boils at a lower level by reducing the pressure of the coolant, thereby increasing the cooling capacity of the cooling tubes.

FIGS. 3C and 6 show a further embodiment wherein the annular catalyst bed is divided into zones of uneven size. In the previously described embodiment shown in FIG. 3B, the catalyst bed was subdivided into three reaction chambers 21B, 22B and 23B of equal size by the partition walls 25B, 26B and 27B. In the present embodiment shown in FIG. 3C, the catalyst bed is divided into three reaction chambers of unequal size in a similar manner. Illustration of the cooling tubes 2C is omitted from FIG. 3C, and also from FIG. 3D discussed below, because the arrangement thereof is essentially the same as shown in FIGS. 3A and 3B. As shown in FIGS. 3C and 6, the synthesis gas flows successively through the inlet 19C, inner gas flow passage 14C, first reaction chamber 21C, first outer flow passage 30C, second reaction 22C, second inner flow passage 32C, third reaction chamber 23C, second outer gas flow passage 15C, and product gas outlet 20C. As indicated by the arrows in FIG. 3C, the gas flow pattern in this embodiment is essentially the same as the flow pattern described for FIG. 3B.

FIGS. 3D and 7 show another embodiment of a reactor useful in the present invention wherein the annular catalyst bed is subdivided in essentially the same manner as shown in FIG. 3B, except that four partition walls 25D, 26D, 27D, 33D are used to define four reaction chambers of equal size 21D, 22D, 23D, 24D. In this embodiment the synthesis gas flows successively through the inlet 19D, inner flow passage 14D, first reaction chamber 21D, first outer gas flow passage 30D, second reaction chamber 22D, second inner gas flow passage 32D, third reaction chamber 23D, second outer gas flow passage 31D, fourth reaction chamber 24D, third inner gas flow passage 15D, and gas outlet 20D. In this embodiment, the gas inlet 19D and outlet 20D can be located side by side near the center of the reactor on the top or bottom face thereof, particularly on the top thereof as shown in FIG. 7. In another embodiment, the gas inlet and outlet may be located apart from each other in the vertical direction.

As shown by the foregoing embodiments, the process of the present invention can be carried out using a radial flow reactor wherein the catalyst bed is subdivided to form a plurality of reaction chambers containing equal or unequal amounts of catalyst. Further, a separate liquid coolant circulation system can be used for each reaction chamber so that the same or different pressures can be employed in the different reaction chambers.

In carrying out the process according to this invention, it is important to select a suitable catalyst bed temperature and a suitable ratio of the molar amount per unit time of the recycle gas relative to the molar amount per unit time of the fresh feed gas, which ratio is hereinafter called the recirculation ratio. The selection of particular temperatures and recirculation ratios depends mainly on the content of carbon monoxide in the fresh feed gas. For example, when the feed gas contains 20 mole percent or less of carbon monoxide, the recirculation ratio should preferably be 2 or less, because the evolution of heat caused by the methanation reaction is relatively mild. In such a case, a relatively low temperature of 240° C.–380° C. can be employed as the catalyst bed temperature when it is desired that the carbon monoxide content of the product gas be 0.1 mole percent or less. A relatively high temperature in the range of 450° C.–550° C. for the catalyst bed can be employed when a carbon monoxide content in the product gas of 2 mole percent or more is desired. In addition, if the desired carbon monoxide content for the product gas lies in the range of 0.1 to 2.0 mole percent, an intermediate temperature range, preferably 380° C.–450° C., can be employed.

When the feed gas contains more than 20 mole percent carbon monoxide, the preferred recirculation ratio is in the range of 3 to 5 and the carbon monoxide content of the product gas can be adjusted by selection of the catalyst bed temperature as described above. In addition, the temperature of the fresh feed gas can be adjusted so that the temperature at the inlet of the catalyst bed is in the range of 240° C.–260° C. in accordance with the selected recirculation ratio as described above, the temperature of the ejector described below, and similar considerations.

In the practice of this invention, the reaction should be effected in the presence of steam when the molar ratio of hydrogen to carbon monoxide in the gas at the inlet of the reactor is 3 or less. In other words, as indicated by the previously described equation (1), in order to convert a large part of the carbon monoxide to methane by the methanation reaction, the stoichiometric molar amount of hydrogen required is at least 3 times the molar amount of carbon monoxide present. The amount of hydrogen is accordingly deficient if the molar ratio of $H_2/CO$ in the inlet gas entering the reactor is less than 3. In such a case, the methanation reaction can be effectively performed by producing hydrogen from carbon monoxide and water in accordance with the reaction (3) above by addition of steam to the feed gas and/or the recirculated gas. In this case the preferred amount of steam is in the range of 1 to 5 moles of steam per mole of carbon monoxide in the synthesis gas (mixture of feed gas and recirculated product gas) at the inlet of the reactor. The presence of steam in the gas at the reactor inlet advantageously maintains the temperature of the catalyst bed at a low level, since the steam dilutes the synthesis gas to some extent. However, even where a synthesis gas having a $H_2/CO$ ratio of 3 or more is introduced at the inlet to the catalyst bed, it is often desirable to effect the methanation reaction in the presence of a relatively small amount of steam effective to prevent the deposition of carbon onto the catalyst due to the decomposition of carbon monoxide.

According to the invention, the product gas is recycled and mixed with the feed gas at a molar recirculation ratio of the recycled product gas to the feed gas may be 0.2 or larger.

When the invention is conducted under such a condition, the following will be further explained. When a molar ratio of hydrogen gas to carbon monoxide is 3 or larger at an inlet of a reactor, the recycled product gas contains steam which has been produced with the reactions shown in the before mentioned chemical equations (1) and (2). The steam which has been recycled this way is contained in an amount enough to prevent carbon from deposition on the catalyst. In this case the carbon deposition can be prevented by the presence of at least 1/5 mole, per 1 mole of carbon monoxide, of steam in the synthesis gas. Accordingly supplemental steam would not be needed.

When a ratio of hydrogen gas to carbon monoxide is less than 3 at the inlet, it is required to add further steam and eventually proceed with the reaction of the chemical equation (3) to the right side, whereby carbon deposition can be prevented.

As the catalyst for the methanation reaction carried out in the process of this invention, known catalysts effective for methanation according to the reactions (1) and (2) can be used. Most such catalysts are also capable of promoting the reaction according to the foregoing equation (3). If such a catalyst is used, no special means for promoting the reaction (3) need be used. If the methanation catalyst is one incapable of promoting the reaction of the equation (3), the reaction of the equation (3) can be promoted by mixing the methanation catalyst with a catalyst for the reaction (3), preferably in a selected reaction chamber of a multi-chamber reactor, thereby supplying additional hydrogen for the reactions (1) and (2).

If it is not feasible to employ a mixed catalyst as described above, one or two additional gas permeable catalyst retainers can be installed, for example, in the space between the catalyst retainers 9, 10 of FIG. 1, and the catalyst for promoting the reaction of the equation (3) can be packed separately from the other catalyst between the catalyst retainers 9 and 10. Preferably, the separate catalyst bed defined by the additional catalyst retainer(s) effects the reaction of the equation (3) prior to the reactions (1) and (2). If two additional catalyst retainers are employed, the catalyst for the reaction of the equation (3) can be packed in the annular intercylinder space formed between the two additional catalyst retainers, so that the methanation reaction is first partially effected, then the supply of hydrogen is increased by the reaction of the equation (3) as the synthesis gas flows through the intermediate catalyst bed, and then the methanation reaction is completed. A similar result can be obtained by employing a reactor having a plurality of reaction chambers, such as those shown in FIGS. 3B, 3C and 3D. The catalyst for the reaction of equation (3) is packed in the entirety of the first reaction chamber or a portion thereof nearest the inlet of the synthesis gas, or in one of the subsequent reaction chambers, so that the methanation reaction is effected while the reaction of equation (3) is used to produce additional hydrogen.

Catalysts useful for promoting the methanation reaction include metallic nickel, molybdenum and other metals with similar catalytic properties. Such catalysts are preferably employed together with a promoter selected from iridium, zirconium, ruthenium and similar elements. Catalysts for the reaction of the equation (3) include iron, zinc, chromium, and copper. The foregoing catalysts are generally employed in granular or pellet form, or the catalyst metal can be deposited on particles of an inert carrier.

According to this invention, the process described in FIG. 1 can be duplicated in a second reactor and the reaction can be carried out in series to form a two-stage reaction system as commonly used in the conventional processes. In practice, however, there is no need for such a two-stage reaction system for carrying out the methanation reaction according to the present invention, and a product gas containing a very small amount of carbon monoxide can be obtained by a one-stage reaction using a single reactor. Consequently, the process for carrying out a methanation reaction according to the present invention is very simple, and the cost of a process plant for carrying out the process of the present invention is lower than comparable costs for conventional processes. Such simplicity, as obtained by the high efficiency of the process of the invention, is the first main advantage of the present invention.

The second advantage of the present invention is that it allows recovery of a large part of the reaction heat in the form of high pressure vapor of the liquid coolant, which heat is available because there is no need to cool the recirculated gas. In the conventional processes, only a relatively small amount of heat can be recovered by heat exchange, taking into account the necessary cooling of the recirculated gas, and as such the conventional processes cannot recover as large an amount of heat as the present invention.

A third advantage of the present invention is that the overall coefficient of heat transfer of the cooling tubes can be increased as described above by using a catalyst bed wherein the synthesis gas passes essentially perpendicularly to the longitudinal direction of the cooling tubes which extend vertically through the catalyst bed of the reactor. This allows the number of total cooling tubes to be reduced, thereby facilitating the structural arrangement of the tubes, and the thickness of the catalyst bed in the direction of gas flow can also easily be reduced. In consequence, the pressure drop is lower when the synthesis gas is flowed through the catalyst bed, thus conserving the power required to operate the booster used to effect circulation of the synthesis gas.

A fourth advantage of the present invention is that the catalyst bed temperature can be maintained at a lower level than in the conventional processes, so that less expensive steel can be used for constructing the reactor. The invention allows the temperature of the catalyst bed to be maintained at 350° C.–380° C. even when the carbon monoxide content in the feed gas exceeds 50 mole percent, because cooling tubes having a very strong cooling effect are present in the catalyst bed. Consequently, whereas expensive materials, such as stainless steel, have been required to construct the reactors used in the conventional processes, a reactor used to carry out the process of the present invention can be constructed using an inexpensive steel, such as a conventional low carbon steel or a low alloy steel containing several percent of at least one element selected from the group consisting of nickel, chromium, manganese, molybdenum and other known alloying elements. Even so, the inner surfaces of the reactor, pipings and the like used in the process of the present invention are preferably covered by a layer of a metal having no detrimental catalytic properties, for the purpose of preventing rust.

As the liquid coolant used in the present invention, it is preferred to use substances having a boiling point in the range of 80° C.–300° C. at atmospheric pressure and which are liquid at normal ambient temperatures. Such substances include water, a mixture of diphenyl and diphenyl oxide, chlorinated hydrocarbons, petroleum hydrocarbon fractions, and mixtures thereof.

The high pressure vapor of the liquid coolant produced by the process of the invention can be effectively utilized by introducing it into a turbine, either directly or after super-heating, in order to generate power. When an organic coolant having a high boiling point is used as the liquid coolant, a heat exchanger can be provided outside of the reactor used in the present invention wherein the coolant undergoes heat exchange with water, thereby producing a high pressure saturated steam which is introduced into a turbine directly or after preheating, thereby generating power. Alternatively, the coolant vapor can be used to preheat the feed gas and supplemental liquid coolant used in the process of the invention. Finally, the coolant vapor can also be used as a heat source for heating materials used in a different process.

According to the invention, the feed gas contains from larger than 5 mol % to 70 mol % of carbon monoxide. The feed gas may also contain hydrogen, carbon dioxide, nitrogen, methane, hydrocarbons other than methane which are gaseous at room temperature, and the like.

As the booster for pressurizing the mixture of the feed gas and the recirculated product gas, a reciprocating or centrifugal compressor or blower can be used, or a booster having no moving parts such as an ejector can be used. If a reciprocating or centrifugal booster is used, the temperature of the gas at the outlet of the catalyst bed is preferably maintained at a low level. If an ejector is used, the driving fluid may be the feed gas, the steam to be mixed therewith, or a mixture thereof. The methanation reaction according to the present invention can be carried out at synthesis gas pressures in the range of 0–100 kg/cm$^2$G.

EXAMPLE

A methanation reaction according to the present invention was carried out using a reaction system as shown in FIG. 1, except that the reactor was the one disclosed in FIG. 4B of U.S. Ser. No. 530,298, referred to above, wherein an annular catalyst bed was divided into two reaction chambers by a vertical partition wall. Water was used as the liquid coolant. The reactor was made of steel containing 0.5 weight percent of molybdenum. The essential dimensions of the reactor were as follows:

| | |
|---|---|
| outer diameter of inner catalyst retainer | 200 mm |
| inner diameter of outer catalyst retainer | 1572 mm |
| outer diameter of cooling tube | 47.2 mm |
| number of coaxial circles on which cooling tubes are arranged | 9 |
| effective length of cooling tube | 4000 mm |

Four cubic meters of a commercially available nickel catalyst was packed in the reactor for the test. The particles of the catalyst were of cylindrical shape 5 mm in both diameter and length. An ejector driven by the feed gas was used as the booster 12 at a recirculation ratio (moles recirculated gas/moles feed gas) of 3. Other process conditions and the results obtained were as follows:

| | |
|---|---|
| Temperature of feed gas | 224° C. |
| Pressure of feed gas | 32.1 kg/cm$^2$G |
| Amount of feed gas supplied | 10,000 Nm$^3$/hr |
| Composition of feed gas mol. %: | |
| carbon monoxide | 26.2% |
| carbon dioxide | 3.4% |
| hydrogen | 54.4% |
| methane | 15.7% |
| water vapor | 0.0% |
| nitrogen | 0.3% |
| Reactor inlet gas pressure | 29.8 kg/cm$^2$G |
| Reactor inlet gas temperature | 350° C. |
| Reactor inlet gas volume | 40,000 Nm$^3$/hr |
| Reactor inlet gas composition (mol. %): | |
| carbon monoxide | 6.62% |
| carbon dioxide | 12.89% |
| hydrogen | 14.94% |
| methane | 48.19% |
| water vapor | 16.91% |
| nitrogen | 0.45% |
| Reactor outlet gas pressure | 29.69 kg/cm$^2$G |
| Reactor outlet gas temperature | 380° C. |
| Reactor outlet gas volume | 36,026 Nm$^3$/hr |
| Reactor outlet gas composition (mol. %): | |
| carbon monoxide | 0.09% |
| carbon dioxide | 16.06% |
| hydrogen | 1.78% |
| methane | 59.02% |
| water vapor | 22.55% |
| nitrogen | 0.50% |
| Pressure difference between inlet and outlet of catalyst bed | 0.11 kg/cm$^2$/G |
| Circulating gas volume | 30,000 Nm$^3$/hr |
| Circulating gas composition | same as reactor outlet gas composition |
| Product gas volume | 6,026 Nm$^3$/hr |
| Product gas composition | Same as reactor outlet gas composition |
| Cooling water system: | |
| cooling water pressure | 106 kg/cm$^2$G |
| make-up cooling water temperature | 120° C. |
| recovered steam pressure | 106 kg/cm$^2$G |
| recovered steam volume | 9277 kg/hr |

Although the invention has been fully described, it will be apparent to one of ordinary skill in the art that many changes and modifications can be made thereto without departing from the spirit or scope of the invention as set forth herein.

The embodiments of the invention in which an exclusive property or privilege is claimed are defined as follows:

1. In a process for producing a methane-containing gas by contacting a methane synthesis gas comprising hydrogen and carbon monoxide with a methanation catalyst at an elevated temperature within a fixed catalyst bed of a methanation reactor, the improvement which comprises:

flowing said synthesis gas substantially horizontally through said catalyst bed, the flow of said synthesis gas being substantially perpendicular to the longitudinal directions of a plurality of vertically extending cooling tubes which extend through said catalyst bed;

flowing a liquid coolant at the boiling temperature thereof under pressure upwardly through said cooling tubes;

collecting a reaction product gas containing methane from an outlet of said catalyst bed; and recirculating, without cooling, a portion of said product gas and mixing said portion of said product gas with a fresh feed gas containing hydrogen and carbon monoxide, the molar amount of said product gas to be mixed with said feed gas being less than 5 times the molar amount of said feed gas; and feeding the mixture of said feed gas and said recirculated product gas into said catalyst bed as said synthesis gas.

2. A process as claimed in claim 1, further comprising operating a turbine with high pressure vapor of said coolant, said high pressure coolant vapor being generated by absorption of methanation reaction heat in said catalyst bed.

3. A process as claimed in claim 1, further comprising mixing steam with said fresh feed gas.

4. A process as claimed in claim 3, wherein said feed gas comprises a gaseous mixture of hydrogen, carbon monoxide, and carbon dioxide.

5. A process as claimed in claim 4, wherein said feed gas contains not more than 20 mole percent of carbon monoxide, the ratio of said molar amount of said recirculated product gas to the molar amount of said fresh feed gas is not greater than 2, and the temperature of said synthesis gas and said catalyst bed remains within the range of 240° C. to 380° C.

6. A process as claimed in claim 4, wherein said feed gas contains more than 20 mole percent carbon monoxide, the ratio of the molar amount of said recirculated product gas to the molar amount of said feed gas is in the range of 3 to 5, and the temperature of said synthesis gas and said catalyst bed remains within the range of 240° C. to 550° C.

7. A process as claimed in claim 4, wherein the molar amount of said steam is in the range of 1 to 5 times the molar amount of carbon monoxide present in said synthesis gas at the inlet of said catalyst bed.

8. A process as claimed in claim 4, wherein said catalyst bed further contains a second catalyst effective to catalyze the reaction of carbon monoxide and water to produce carbon dioxide and hydrogen.

9. A process as claimed in claim 4, wherein said catalyst comprises a metal selected from the group consisting of nickel and molybdenum.

10. A process as claimed in claim 8, wherein said second catalyst is a metal selected from the group consisting of iron, zinc, chromium and copper.

11. A process as claimed in claim 4, wherein said liquid coolant has a boiling point in the range of 80° C. to 300° C. under atmospheric pressure and is liquid at room temperature.

12. A process as claimed in claim 11, wherein said liquid coolant is selected from the group consisting of water, a mixture of diphenyl and diphenyl oxide, chlorinated hydrocarbons, petroleum hydrocarbon fractions and mixtures thereof.

13. A process as claimed in claim 11, wherein the temperature of said synthesis gas and the temperature of said catalyst bed remain within the range of 240° C. to 600° C., the pressure of said synthesis gas is in the range of 0 to 100 kg/cm$^2$G, and said feed gas contains from more than 5 to not more than 70 mole percent of carbon monoxide.

14. A process as claimed in claim 8, wherein said methanation catalyst and said second catalyst are mixed together in said catalyst bed.

15. A process as claimed in claim 8, wherein said catalyst bed is subdivided into first and second adjacent catalyst beds, one of said first and second beds containing said methanation catalyst, and the other of said first and second beds containing said second catalyst.

16. A process as claimed in claim 4, wherein said catalyst bed is of annular shape, and said synthesis gas is flowed alternately radially inwardly and outwardly relative to a central vertical axis of said catalyst bed through a series of reaction chambers of said catalyst bed, said reaction chambers being formed by subdividing said catalyst bed with radial partition walls.

* * * * *